US012036365B2

(12) United States Patent
Drew et al.

(10) Patent No.: US 12,036,365 B2
(45) Date of Patent: Jul. 16, 2024

(54) ENDOTRACHEAL TUBE HOLDER DEVICE

(71) Applicant: TELEFLEX MEDICAL INCORPORATED, Morrisville, NC (US)

(72) Inventors: Douglas Drew, Raleigh, NC (US); Daniel P. Dwyer, Cary, NC (US); Christopher S. Jackson, Knightdale, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 819 days.

(21) Appl. No.: 16/980,118

(22) PCT Filed: Mar. 15, 2019

(86) PCT No.: PCT/US2019/022466
§ 371 (c)(1),
(2) Date: Sep. 11, 2020

(87) PCT Pub. No.: WO2019/178477
PCT Pub. Date: Sep. 19, 2019

(65) Prior Publication Data
US 2021/0008315 A1 Jan. 14, 2021

Related U.S. Application Data

(60) Provisional application No. 62/644,177, filed on Mar. 16, 2018.

(51) Int. Cl.
*A61M 16/00* (2006.01)
*A61B 90/50* (2016.01)
(Continued)

(52) U.S. Cl.
CPC ......... *A61M 16/0497* (2013.01); *A61B 90/50* (2016.02); *A61B 90/57* (2016.02);
(Continued)

(58) Field of Classification Search
CPC .......... A61M 16/0497; A61M 16/0461; A61M 16/04; A61M 16/0493; A61M 16/0688;
(Continued)

(56) References Cited

U.S. PATENT DOCUMENTS 3,713,448 A 1/1973 Arrott
3,756,244 A 9/1973 Kinnear et al.
(Continued)

FOREIGN PATENT DOCUMENTS

CN 1750854 A 3/2006
CN 104039379 A 9/2014
(Continued)

OTHER PUBLICATIONS

Intubix Endotracheal Tube Holder on youtube.com dated Dec. 4, 2009, https://www.youtube.com/watch?v=Oeevu8nZOPo (Year: 2009).
(Continued)

*Primary Examiner* — Michael R Reid
*Assistant Examiner* — Sarah B Lederer
(74) *Attorney, Agent, or Firm* — BakerHostetler (57) ABSTRACT

An endotracheal tube holder device is provided for securely holding an endotracheal tube to a patient during intubation. The tube holder device includes a support rail placed above a lip of a patient. An auxiliary clip is coupled to the support rail and slidably movable along the length of the support rail for holding an accessory device relative to the patients face. The auxiliary clip includes both a horizontal accessory clip and a vertical accessory clip to releasably retain the accessory device horizontally and vertically, respectively. A tube fastener is coupled to the support rail and includes a tube
(Continued)

holder base, an adjustment clip coupled to the tube bolder base for laterally repositioning the tube holder base along the support rail, and a securement tie. The securement tie may be wrapped around a portion of the endotracheal tube to secure the tube to the tube holder base.

20 Claims, 10 Drawing Sheets (51) Int. Cl.
A61B 90/57 (2016.01)
A61M 16/04 (2006.01)
A61M 16/06 (2006.01)

(52) U.S. Cl.
CPC .... *A61M 16/0461* (2013.01); *A61M 16/0493* (2014.02); *A61M 16/0688* (2014.02); *A61B 2090/508* (2016.02)

(58) Field of Classification Search
CPC ........ A61M 25/02; A61B 90/50; A61B 90/57; A61J 15/00; A61J 15/0015; A61J 15/0053
See application file for complete search history.

(56) References Cited

U.S. PATENT DOCUMENTS

| | | | |
|---|---|---|---|
| 3,924,636 A | 12/1975 | Addison | |
| 3,946,742 A | 3/1976 | Eross | |
| 4,191,180 A | 3/1980 | Colley et al. | |
| 4,270,529 A | 6/1981 | Muto | |
| 4,282,871 A | 8/1981 | Chodorow | |
| 4,326,515 A | 4/1982 | Shaffer et al. | |
| 4,351,331 A | 9/1982 | Gereg | |
| 4,449,527 A | 5/1984 | Hinton | |
| 4,683,882 A | 8/1987 | Laird | |
| 4,744,358 A | 5/1988 | McGinnis | |
| 4,774,944 A | 10/1988 | Mischinski | |
| 4,832,019 A | 5/1989 | Weinstein et al. | |
| 4,867,154 A | 9/1989 | Potter et al. | |
| 4,906,234 A | 3/1990 | Voychehovski | |
| 5,009,227 A | 4/1991 | Nieuwstad | |
| 5,020,534 A | 6/1991 | Pell et al. | |
| 5,076,269 A | 12/1991 | Austin | |
| 5,117,818 A * | 6/1992 | Palfy .................... | A61M 25/02 128/207.18 |
| 5,341,802 A | 8/1994 | Calebaugh | |
| 5,345,931 A | 9/1994 | Battaglia, Jr. | |
| 5,395,343 A | 3/1995 | Iscovich | |
| 5,419,319 A | 5/1995 | Werner | |
| 5,437,273 A | 8/1995 | Bates et al. | |
| 5,479,921 A | 1/1996 | Reif | |
| 5,490,504 A | 2/1996 | Vrona et al. | |
| 5,513,633 A | 5/1996 | Islava | |
| 5,551,421 A | 9/1996 | Noureldin et al. | |
| 5,555,881 A | 9/1996 | Rogers et al. | |
| 5,649,534 A | 7/1997 | Briggs, III | |
| 5,829,430 A | 11/1998 | Islava | |
| 6,010,484 A | 1/2000 | McCormick et al. | |
| 6,050,263 A | 4/2000 | Choksi et al. | |
| 6,067,985 A | 5/2000 | Islava | |
| 6,105,577 A | 8/2000 | Varner | |
| 6,408,850 B1 | 6/2002 | Sudge | |
| 6,561,192 B2 | 5/2003 | Palmer | |
| 6,578,576 B1 | 6/2003 | Taormina et al. | |
| 6,634,359 B1 | 10/2003 | Rudy, Jr. et al. | |
| 6,810,878 B2 | 11/2004 | Palmer | |
| 7,017,579 B2 | 3/2006 | Palmer | |
| 7,063,088 B1 | 6/2006 | Christopher | |
| 7,231,921 B2 | 6/2007 | Palmer | |
| 7,896,004 B2 | 3/2011 | Yang | |
| 8,096,300 B2 | 1/2012 | Russo | |
| 8,156,934 B2 | 4/2012 | Trodler | |
| 8,256,427 B2 | 9/2012 | Chang et al. | |
| 8,302,597 B2 | 11/2012 | Beely et al. | |
| 8,636,008 B2 | 1/2014 | Flory et al. | |
| 8,726,903 B2 | 5/2014 | Levine | |
| 8,857,434 B2 * | 10/2014 | Han ...................... | A61M 25/02 128/207.11 |
| 9,233,221 B2 | 1/2016 | Haider et al. | |
| 9,308,340 B2 | 4/2016 | Bond et al. | |
| 9,381,315 B2 | 7/2016 | Chin | |
| 9,707,364 B2 * | 7/2017 | Islava ............... | A61M 16/0497 |
| D804,659 S | 12/2017 | Hood | |
| 9,981,101 B2 | 5/2018 | VanMiddendorp et al. | |
| 10,888,680 B2 | 1/2021 | Zickefoose et al. | |
| 2005/0133038 A1 | 6/2005 | Rutter | |
| 2007/0299358 A1 | 12/2007 | Bertinetti et al. | |
| 2010/0083970 A1 | 4/2010 | Beely et al. | |
| 2011/0240034 A1 | 10/2011 | Ciccone | |
| 2012/0168571 A1 | 7/2012 | Bond et al. | |
| 2012/0227747 A1* | 9/2012 | Levine .................. | A61M 25/02 128/207.14 |
| 2013/0068233 A1 | 3/2013 | De Lulio et al. | |
| 2014/0238406 A1 | 8/2014 | Borre et al. | |
| 2014/0261462 A1* | 9/2014 | Visconti .................. | A61C 5/90 128/861 |
| 2014/0261463 A1 | 9/2014 | Visconti et al. | |
| 2015/0018759 A1 | 1/2015 | Velez-Rivera | |
| 2015/0090255 A1* | 4/2015 | Gulliver ............. | A61J 15/0061 604/179 |
| 2016/0095995 A1 | 4/2016 | Haider et al. | |
| 2016/0121067 A1 | 5/2016 | VanMiddendorp et al. | |
| 2016/0235935 A1 | 8/2016 | Mirza et al. | |
| 2016/0271349 A1* | 9/2016 | Zickefoose ....... | A61M 16/0497 |
| 2016/0279367 A1 | 9/2016 | Kanowitz | |
| 2016/0361509 A1 | 12/2016 | Blessing, Jr. et al. | |
| 2017/0173288 A1 | 6/2017 | Stam et al. | |
| 2017/0197049 A1 | 7/2017 | Doll | |
| 2018/0099112 A1 | 4/2018 | Belenkiy | |
| 2018/0207381 A1 | 7/2018 | Winthrop et al. | |
| 2020/0222651 A1 | 7/2020 | Jockel et al. | |
| 2021/0187229 A1 | 6/2021 | Brar | |

FOREIGN PATENT DOCUMENTS

| | | |
|---|---|---|
| CN | 105611962 A | 5/2016 |
| GB | 2465621 A | 6/2010 |
| JP | H07-331714 | 12/1995 |
| KR | 100909101 | 8/2008 |
| WO | 2014/144656 A1 | 9/2014 |
| WO | 2015/023358 A1 | 2/2015 |
| WO | 2015127443 | 8/2015 |
| WO | 2016114643 | 7/2016 |
| WO | 2016116916 | 7/2016 |
| WO | 2017145101 | 8/2017 |
| WO | 2017179780 | 10/2017 |
| WO | 2018071804 | 4/2018 |

OTHER PUBLICATIONS

International Preliminary Report on Patentability and Written Opinion issued in PCT/US2019/022466, dated Oct. 1, 2020.
International Search Report of PCT/US2020/050393 dated Dec. 21, 2020, 2 pages.
International Search Report from PCT/US2019/022466; dated Jun. 6, 2019.

* cited by examiner

ENDOTRACHEAL TUBE HOLDER DEVICE

CROSS-REFERENCE TO RELATED APPLICATIONS

The present application is a National Stage of International Patent Application No. PCT/US2019/022466, filed Mar. 15, 2019, which claims priority to U.S. Provisional Patent Application No. 62/644,177, filed Mar. 16, 2018, the contents of which are incorporated herein by reference in their entirety.

FIELD OF THE INVENTION

The present disclosure generally relates to medical device holders, and more particularly to a device for securely holding an endotracheal tube.

BACKGROUND

Endotracheal tubes are often inserted into the trachea of a patient to establish and maintain a patient's airway during resuscitation, anesthesia, and other critical care procedures. Endotracheal tubes help deliver air to patients who cannot breathe on their own volition. They are often placed prior to surgery or are used for critically ill patients that require breathing assistance for extended periods of time. Once inserted, the endotracheal tube must be fastened in a desired fixed position to prevent movement of the endotracheal tube for extended periods of time, including up to several days.

In order to properly secure the endotracheal tube relative to a patient during intubation, conventional endotracheal tube holder devices have are known which use a variety of securement methods. However, in many of these conventional tube holder devices, it is both difficult and time-consuming to secure and release the endotracheal tube before and after intubation, which can cause significant discomfort to the patient. Moreover, most conventional endotracheal tube holder devices do not adequately stabilize the endotracheal tube relative to the patient's face. Accordingly, there is a need for an endotracheal tube holder device having an improved tube holder and stabilization mechanism.

SUMMARY OF THE INVENTION

The foregoing needs are met, to a great extent, by the present disclosure of an endotracheal tube holder apparatus discussed herein. The endotracheal tube holder apparatus may comprise a support rail having opposite ends and an exterior portion defining a plurality of retention grooves at least partially along a length of the support rail between the opposite ends, the support rail configured to be placed above a lip of a patient. An auxiliary clip is coupled to the support rail and slidably movable along the length of the support rail between the opposite ends, the auxiliary clip being configured to hold an accessory device relative to the patient's face. A tube fastener is coupled to the support rail and slidably movable along the length of the support rail between the opposite ends. The tube fastener may include a tube holder base having a first side region and a spaced apart second side region. An adjustment clip is coupled to the tube bolder base, the adjustment clip being configured to releasably engage the exterior portion of the support rail for laterally repositioning the tube holder base along the support rail between the opposite ends. And a securement tie is configured to be wrapped around a portion of the endotracheal tube, the securement tie having a first end region coupled to the first side region of tube holder base, and a second end region configured to secure to the second side region of the tube holder base.

According to another aspect of the disclosure, the auxiliary clip further comprises a clip base having a front surface defining an opening configured to receive the accessory device.

According to another aspect of the disclosure, the auxiliary clip further comprises a clip base having a front surface defining an opening configured to receive the accessory device.

According to another aspect of the disclosure, the clip base further includes a horizontal accessory clip and a vertical accessory clip configured to releasably retain the accessory device horizontally and vertically, respectively.

According to another aspect of the disclosure, the horizontal accessory clip includes a first horizontal accessory clip portion and a second horizontal accessory clip portion, the first horizontal accessory clip portion being larger than the second horizontal accessory clip portion, and the vertical accessory clip includes a first vertical accessory clip portion and a second vertical accessory clip portion, the first vertical accessory clip portion being larger than the second vertical accessory clip portion.

According to another aspect of the disclosure, the auxiliary clip is further configured to stabilize the support rail on the patient's face.

According to another aspect of the disclosure, the auxiliary clip further includes a stabilizer pad configured to contact and adhere to a patient's nose and/or a region of a patient's cheek adjacent to the patient's nose.

According to another aspect of the disclosure, the stabilizer pad comprises a skin contacting surface including a skin compliant adhesive.

According to another aspect of the disclosure, the accessory device is a nasogastric tube.

According to another aspect of the disclosure, the apparatus further comprises a retention clip extending from the second side region of the tube holder base for retaining the securement tie.

According to another aspect of the disclosure, the securement tie further comprises a plurality of teeth disposed between the first and second end regions.

According to another aspect of the disclosure, the securement tie further includes a grip flap disposed between the first end region and the plurality of teeth for pulling the securement tie away from the second side region of the tube holder base.

According to another aspect of the disclosure, the tube holder base further includes a bottom surface configured to engage a portion of the endotracheal tube.

According to another aspect of the disclosure, the bottom surface of the tube holder base includes a plurality of barbs configured to engage the endotracheal tube.

According to another aspect of the disclosure, the bottom surface of the tube holder base defines a substantially V-shaped catch configured to contact the endotracheal tube and minimize displacement of the endotracheal tube relative to the tube holder base.

According to another aspect of the disclosure, the tube fastener further comprises a movable pawl configured to engage at least one of the plurality of teeth of the securement tie to secure the tie around the endotracheal tube.

According to another aspect of the disclosure, the tube holder base further comprises a slot configured to receive the second end region of the securement tie such that the second end region of the securement tie is pulled past the pawl through the slot to secure the endotracheal tube to the tube holder base.

According to another aspect of the disclosure, the apparatus further comprises a fixed grip tab extending from a first side region of the tube holder base and disposed proximate the movable pawl.

According to another aspect of the disclosure, the apparatus further comprises an adhesive tape applied to a first surface of the securement tie at the first end region, wherein the first surface of the tie is configured to contact a portion of the endotracheal tube.

According to another aspect of the disclosure, the tube fastener further comprises a bite block coupled to the tube holder base and configured to extend into a mouth of a patient, and wherein the bite block has a substantially cylindrical shape defining an axial opening along an entirety of a length of the bite block.

According to another aspect of the disclosure, the a kit may comprise an apparatus for holding an endotracheal tube according to the above disclosure, an endotracheal tube, and a nasogastric accessory tube.

There has thus been outlined certain embodiments of the disclosure in order that the detailed description thereof herein may be better understood, and in order that the present contribution to the art may be better appreciated. There are additional embodiments of the disclosure that will be described below and which form the subject matter of the claims appended hereto.

In this respect, before explaining at least one aspect of the endotracheal tube holder device in detail, it is to be understood that the endotracheal tube holder device is not limited in its application to the details of construction and to the arrangements of the components set forth in the following description or illustrated in the drawings. The endotracheal tube holder device is capable of aspects in addition to those described, and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the endotracheal tube holder device. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the endotracheal tube holder device are illustrated by way of examples in the accompanying drawings.

DETAILED DESCRIPTION

Figure 1:
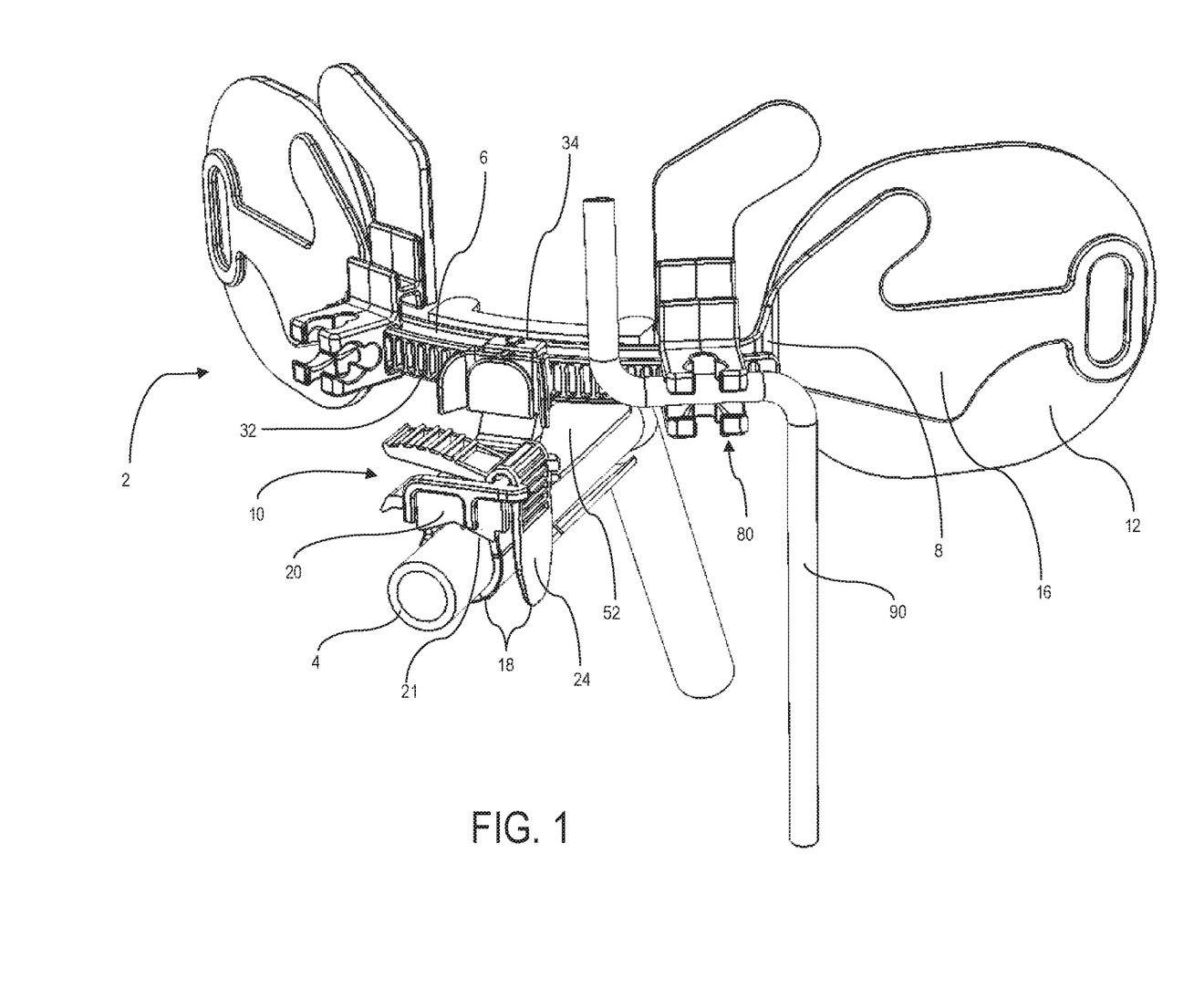
FIG. 1 is a perspective view of an endotracheal tube holder device holding an endotracheal tube and an accessory tube according to the present disclosure.
Figure 2:
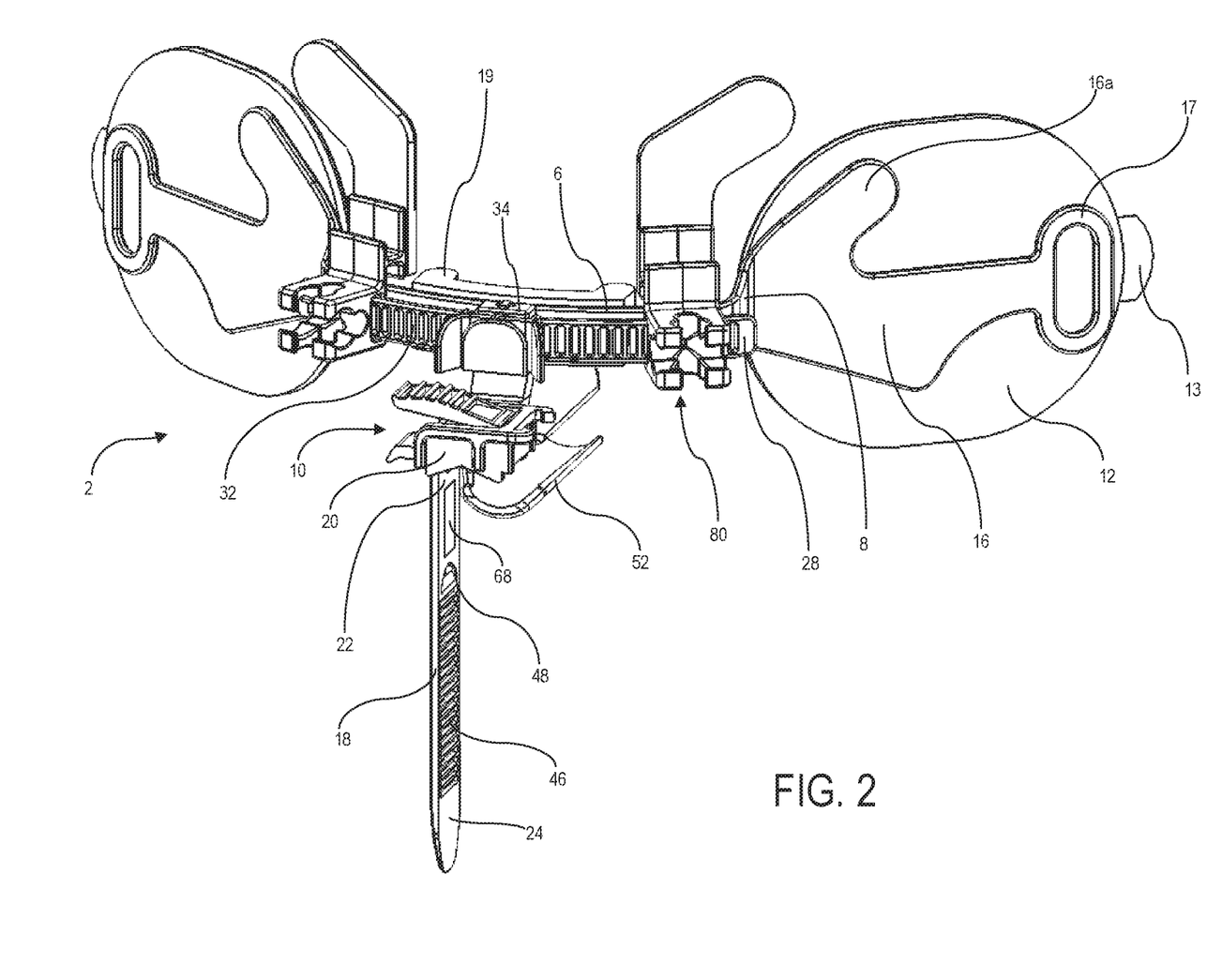
FIG. 2 is a perspective view of the endotracheal tube holder device of FIG. 1 without an endotracheal tube and an accessory tube.
Figure 3:
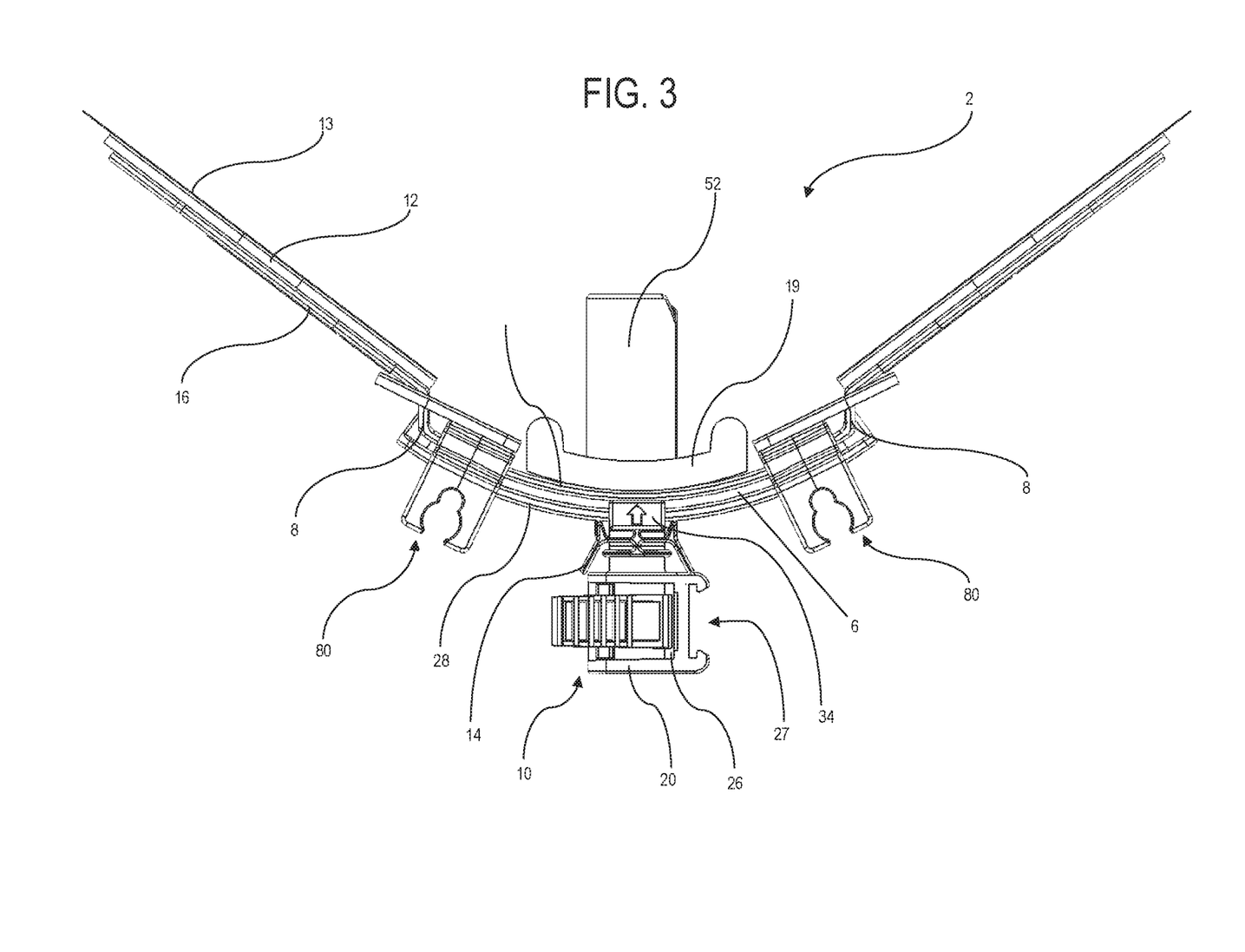
FIG. 3 is a top plan view the endotracheal tube holder device of FIG. 2.
Figure 4:
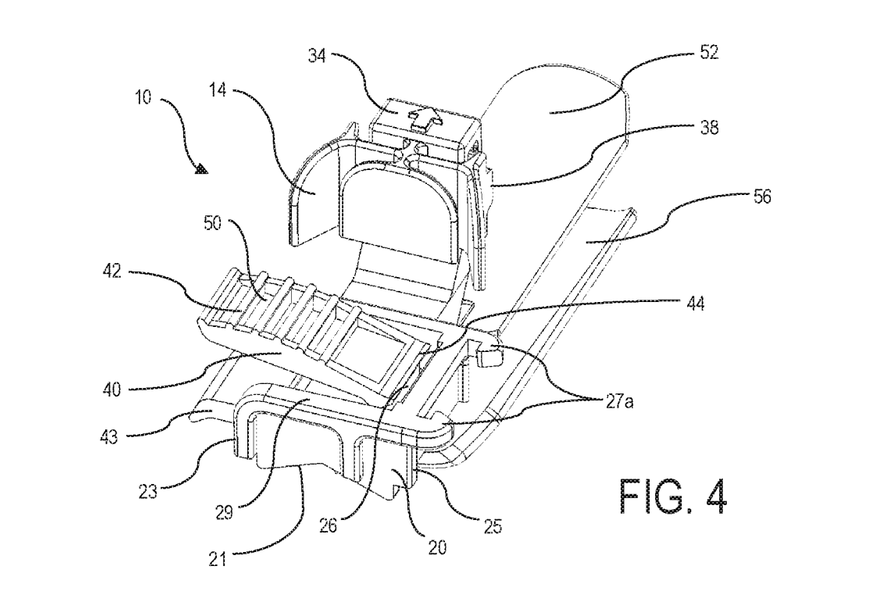
FIG. 4 is a top perspective view of a tube fastener in accordance with the present disclosure.
Figure 5:
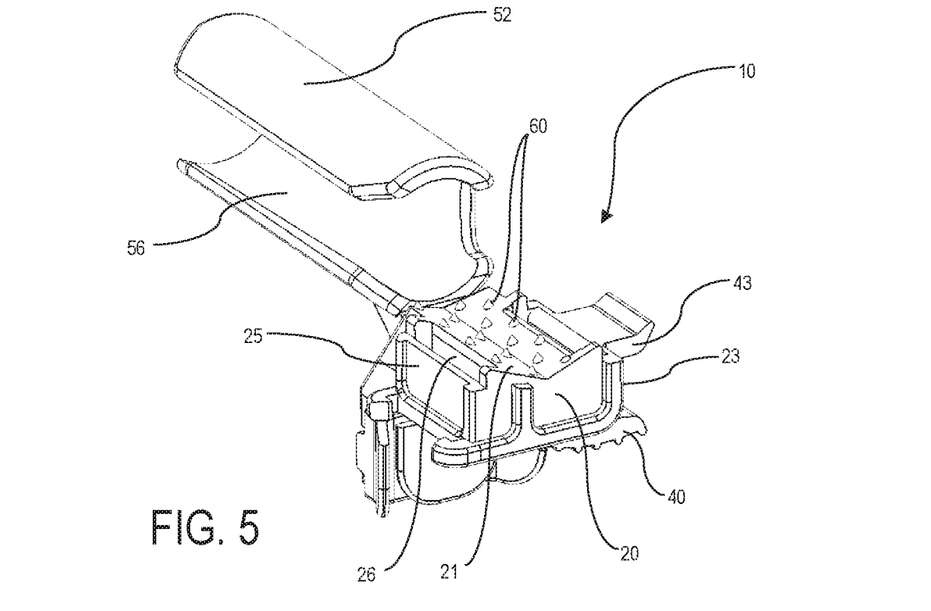
FIG. 5 is a bottom perspective view of the tube fastener in accordance with the present disclosure.
Figure 6:
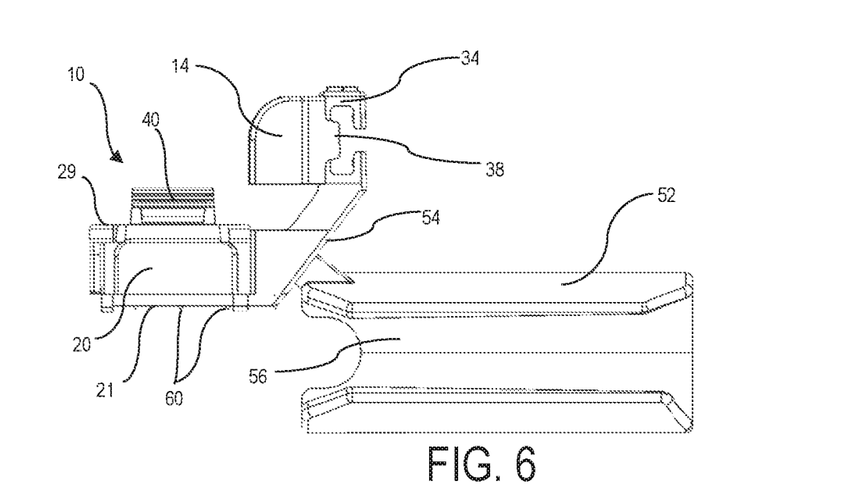
FIG. 6 is a side elevation view of the tube fastener in accordance with the present disclosure.
Figure 7:
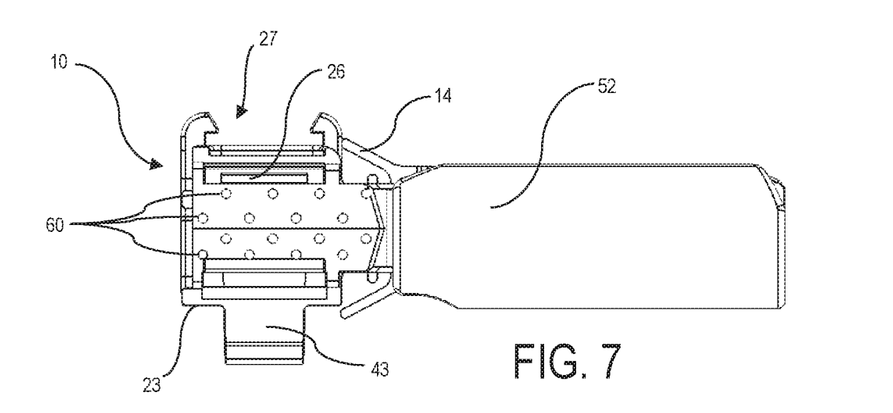
FIG. 7 is a bottom plan view of the tube fastener in accordance with the present disclosure.
Figure 8:
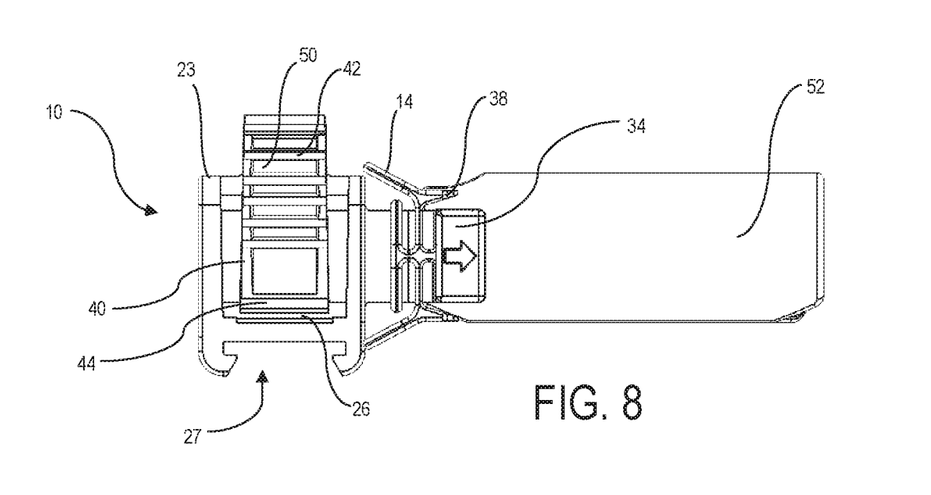
FIG. 8 is a top plan view of the tube fastener in accordance with the present disclosure.

FIGS. 1-3 illustrate an endotracheal tube holder device 2 configured to secure an endotracheal tube 4 to a patient during intubation. The endotracheal tube holder device 2 includes a curved support rail 6 configured to fit across a patient's face above the patient's upper lip. More specifically, the support rail 6 is configured to lie substantially horizontal across the patient's face. The rail 6 includes an exterior portion 28, an interior portion 30, and two opposite ends 8, wherein each opposite end 8 of the rail 6 is connected to a respective cheek support 16. An innerface of each cheek support 16 is coupled to a corresponding cheek pad 12 configured to contact the patient's cheek. The cheek pads 12 may be provided in various sizes to accommodate patients of various sizes. The cheek pads may further be provided in protective packaging.

The cheek pads 12 may be made of a hydrocolloid dressing, foam, a combination thereof, or some other skin compatible dressing. Each cheek pad 12 includes a skin contacting surface that may have an adhesive applied thereto to improve adherence of the pads 12 to the patient. Each cheek pad 12 may also include a peelable backing liner 13 to preserve the adhesive when the cheek pads 12 are not adhered to the patient's cheeks. In some implementations, the cheek pads 12 may be flat, and further may be configured to become contoured to match the shape of a patient's face.

Each cheek support 16 may include one or more rail fingers 16a coupled to the respective cheek pad 12 to provide additional support and flexibility. Each cheek support 16 may also include one or more strap loops 17 configured to couple to an adjustable head strap (not shown) for securing the endotracheal tube holder device 2 to a patient's head. A widened generally U-shaped upper lip cushion 19 may be removably adhered to the interior portion 30 of the support rail 6. The upper lip cushion 19 is configured to contact a patient's face in the region between the patient's upper lip and nose to help retain the rail 6 in a desired position against the patient's face during use.

At least one auxiliary clip 80 may be removably attached to the support rail 6. In some implementations, the auxiliary clip 80 is configured to further stabilize the endotracheal tube holder device 2 on the patient's face. In other implementations, the auxiliary clip 80 is configured to hold an accessory device 90, such as a nasogastric tube or other accessory line. In still other implementations, the auxiliary clip 80 is configured to hold an accessory device 90 and also stabilize the endotracheal tube holder device 2 on the patient's face.

The endotracheal tube holder device 2 further includes a tube fastener 10 coupled to and slidable along the support rail 6 between the opposite ends 8 thereof. The tube fastener 10 comprises a securement tie 18, a tube holder base 20, an adjustment clip 34, and a bite block 52. The adjustment clip 34 includes a pair of spaced apart lever arms 14 configured to permit selective lateral repositioning of the tube fastener 10 relative to the support rail 6, as will be discussed in greater detail below. Further, the rail 6 and the adjustment clip 34 may be configured such that the adjustment clip 34 is slidable onto one of the opposite ends 8 of the rail, but not slidable onto the other opposite end of the rail. The rail 6 and the adjustment clip 34 may also be configured such that the adjustment clip 34 is not removable from the rail once the adjustment clip is slid onto the rail. The rail 6 and the tube fastener 10 may both be made from a durable, rigid plastic material, such as polypropylene or polyethylene among others. In some aspects, the rail 6 may be made from a flexible plastic material in order to better curve around the contours of the patient's face.

The endotracheal tube 4 is secured to an underside 21 of the tube holder base 20 via the securement tie 18, as shown in particular in FIG. 1. A first end region 22 of the securement tie 18 is fixedly coupled to a first side region 23 of tube holder base 20 via adhesive, bonding, a friction fit, or clamping, among others. A second end region 24 of the securement tie 18 is wrapped around the endotracheal tube 4 in a first direction (i.e., in a counterclockwise fashion), and inserted through a slot 26 in a second side region 25 of the tube holder base 20. The slot 26 extends from an underside 21 of the tube holder base 20 to an upper side 29 thereof. The second end region 24 of the tie 18 is then tautly pulled upward through the slot 26 of the tube holder base 20, such that the second end region of the tie enters the slot at the underside 21 of the tube holder base and exits the slot from the upper side 29 of the tube holder base.

The second end region 24 of the securement tie 18 is further bent in an opposite second direction (i.e., in a clockwise fashion) over an edge of the second side 25 of the tube holder base 20. The second end region 24 of the tie 18 may further be tautly pulled downward through a retention clip 27 provided at the second side region 25 of the tube holder base 20. The retention clip 27 includes pair of hooks 27a extending from the second side 25 of the tube holder base 20. The retention clip 27 is configured to retain the securement tie 18 tautly around the endotracheal tube 4 in order to keep the endotracheal tube 4 in a fixed position relative to the tube fastener 10.

The tube fastener 10 is coupled to the support rail 6 via the adjustment clip 34. Moreover, since the tube holder base 20 is coupled to the adjustment clip 34, the endotracheal tube 4 may be repositioned laterally along the length of the support rail 6 by actuating the lever arms 14 of the adjustment clip. The exterior surface 28 of the rail 6 includes a plurality of retention grooves 32 configured to engage with the lever arms 14 of the tube fastener 10. The retention grooves 32 may have a variety of shapes, such as, for example, a discorectangular shape as shown in FIGS. 1 and 2. A large number of retention grooves 32 may be provided in order to increase adjustability of the endotracheal tube holder device 2.

Referring to FIGS. 4-9, various views the tube fastener 10 are depicted without the securement tie 18 attached thereto. As illustrated throughout these figures, the tube holder base 20 extends laterally away from the adjustment clip 34 at a substantially perpendicular angle. In some aspects, the specific geometry between the tube holder base 20 and the adjustment clip 34 may vary depending on the desired orientation of the tube fastener 10 relative to the support rail 6.

Each lever arm 14 of the adjustment clip 34 includes a respective retention prong 38 that projects towards the support rail 6. The retention prongs 38 are configured to engage the plurality of retention grooves 32 on the rail 6. When the lever arms 14 are in a resting or non-actuated position, the retention prongs 38 rest within the respective grooves 32 to prevent lateral movement of tube fastener 10 with respect to the support rail 6. The lever arms 14 may be manipulated by laterally compressing or squeezing them toward each other. Thus, when the lever arms 14 are actuated in such a manner, the retention prongs 38 are correspondingly disengaged out of the respective retention grooves 32. As a result, the retention prongs 38 no longer restrict lateral movement of the tube fastener 10 with respect to the support rail 6. Accordingly, actuating the lever arms 14 by pressing them toward each other allows a user to reposition the tube fastener 10 laterally along the support rail 6. Such repositioning may be desirable in situations where medical personnel may want to conduct a procedure around the patient's face or within the patient's mouth without having to remove the endotracheal tube 4 from the tube fastener 10.

The tube fastener 10 further includes a pawl 40 coupled to the tube holder base. The pawl may be, for example, a lever. The pawl 40 and the tube fastener 10 define a slot 26 on a second side region 25 of the tube holder base 20. The pawl 40 may be actuated to increase the size of the slot 26, thus allowing the securement tie 18 to pass through the slot 26 as previously discussed above. The pawl 40 may have a raised region 42 located at the first side region 23 of the tube holder base 20 and a catch region 44 located at the second side region 25 of the tube holder base 20. The thickness of the pawl 40 may taper from the raised region 42 towards the catch region 44. The pawl 40 may be actuated by applying a downward force onto the raised region 42 of the pawl 40, which will correspondingly raise the catch region 44 and increase the size of the slot 26. A plurality of indentations 50 are provided on the pawl 40 to provide tactile indication that allows the patient or practitioner to identify and actuate the raised region 42 of the pawl 40 based on feel.

The tube fastener 10 also includes a grip tab 43 extending laterally from the first side 23 of the tube holder base 20. The grip tab 43 is configured to assist single-handed actuation of the pawl 40. In particular, the grip tab 43 defines a widened base having a downward sloping tail end. During actuation of the pawl 40, a user may apply a downward force onto the raised region 42 of the pawl 40 with a first finger, such as an index finger, while simultaneously placing a second finger, such as a thumb, underneath the grip tab 43 to provide support so that the tube holder base 20 and endotracheal tube 4 do not unintentionally move out of position. Accordingly, this arrangement permits a user to squeeze and move the pawl 40 relative to the stationary grip tab 43 so that the force applied to the pawl is prevented from correspondingly shifting the tube holder base 20, thus keeping the tube holder base and the endotracheal tube in their desired positions relative to the patient's face.

Figure 11:
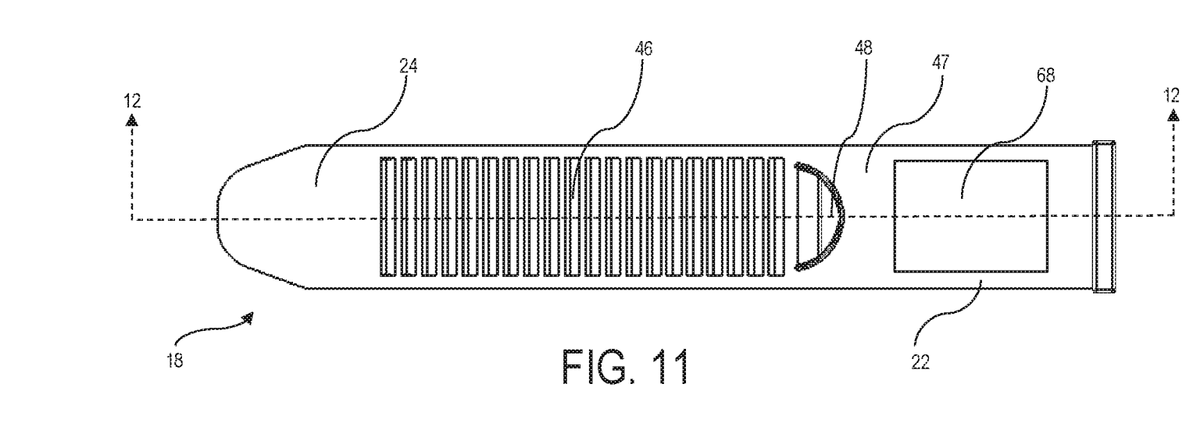
FIG. 11 is a top plan view of a securement tie in accordance with the present disclosure.
Figure 12:
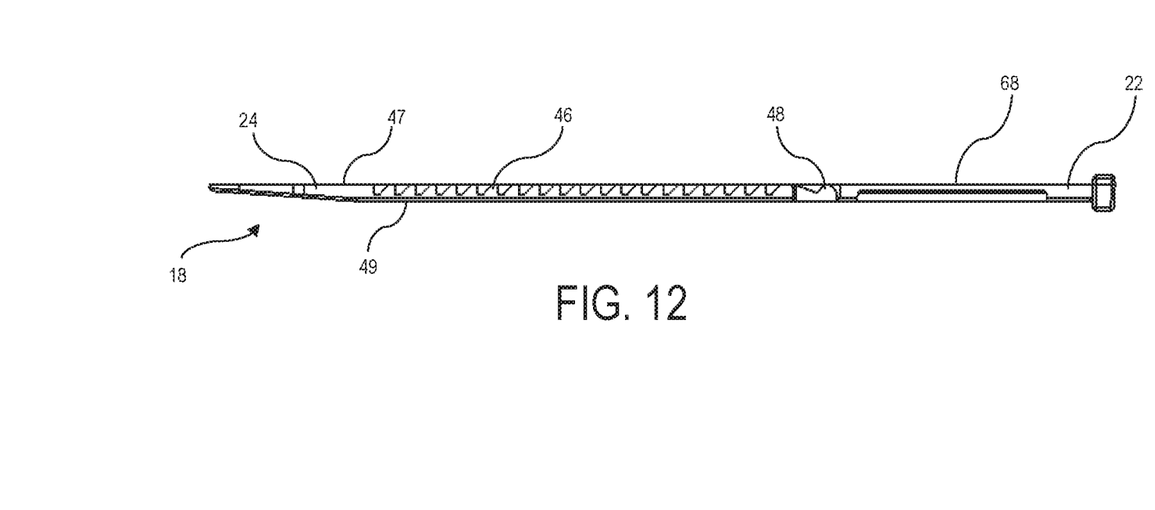
FIG. 12 is a cross-sectional view of the securement tie taken along line 12-12 in FIG. 11.

The first end region 22 of the securement tie 18 is fixed to the first side region 23 of the tube holder base 20 via an adhesive, a fastener, a frictional fit, or a mechanical bond, among other securing means. Turning to FIGS. 11 and 12, the securement tie 18 shown has a plurality of teeth 46 on a first surface 47 of the tie 18. In use, the first surface 47 of the securement tie 18 contacts the endotracheal tube 4 when the tie 18 is wrapped around the endotracheal tube 4 to secure the endotracheal tube 4 to the tube holder base 20, as previously discussed above. The plurality of teeth 46 on the first surface 47 increases the friction between the securement tie 18 and the outer surface of the endotracheal tube 4 to help prevent lateral or rotational movement of the endotracheal tube 4. A strip of tape 68 or other type of adhesive may be applied to the first surface 47 at the first end region 22 of the securement tie 18. The adhesive tape 68 may provide additional securement of the endotracheal tube 4 to the tube holder base 20 and help prevent any lateral or rotational movement of an endotracheal tube 4. The plurality of teeth 46 are located in a middle strip of the tie 18. The teeth 46 are configured to be engaged by the pawl 40 of the tube fastener 10 to secure the endotracheal tube 4.

In some aspects, the plurality of teeth 46 may extend linearly across the width of the tie 18. In other aspects, the teeth 46 may have a different pattern, such as a curve, on the tie 18. The second end region 24 of the securement tie may include a tapered portion to facilitate fit through the slot 26 on the tube holder base 20. Further, the plurality of teeth 46 are disposed on the first surface of the tie 18, wherein the first surface 47 of the tie is configured to contact an outer surface of the endotracheal tube.

In some implementations, the plurality of teeth 46 on the tie 18 may be implemented with different patterns across the width of the tie 18. For instance, a middle strip of the plurality of teeth may have a horizontal pattern across the width of the tie while two side strips adjacent to the middle strip may have a slanted pattern. Other patterns such as curves or waves may be implemented on the middle strip or the side strips. Moreover, the patterns of the plurality of teeth may also vary along the length of the tie in addition to or instead of varying along the width of the tie.

Further, the plurality of teeth 46 may be formed on the tie 18 with different shapes, including a sawtooth wave, a square wave, a rectangular wave, a trapezoidal wave, and a triangular wave, among others. In addition, the plurality of teeth 46 may be formed from a combination of the aforementioned shapes. The plurality of teeth 46 may also be formed within the first surface 47 of the tie 18, or the plurality of teeth may be formed extending from the first surface 47 of the tie 18.

Thus, to secure an endotracheal tube 4 to the tube fastener 10, the endotracheal tube 4 is first placed below the tube holder base 20. The securement tie 18 is then wrapped around the endotracheal tube 4 and the second end region 24 of the tie 18 is inserted into the slot 26 on the tube holder base 20. The pawl 40 and the securement tie 18 act as a ratchet that permits the tie 18 to be pulled upwards through the slot 26 in the tube holder base 20, but restricts movement of the tie 18 in the opposite downward direction. In particular, the catch region 44 of the pawl 40 engages with the plurality of teeth 46 on the tie 18 and clamps down to prevent movement of the tie 18. To fully secure the endotracheal tube 4, the securement tie 18 is pulled taut and wrapped over the edge of the second side 25 of the tube holder base 20 so that a portion of the tie 18 is retained by the pair of hooks 27a of the retention clip 27.

Figure 10:
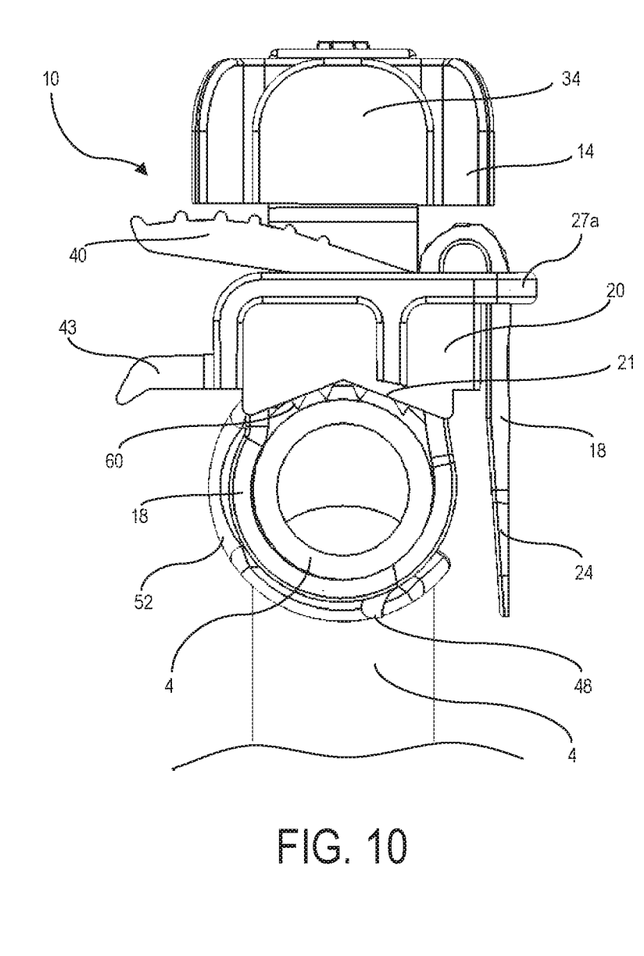
FIG. 10 is a front elevation view of the tube fastener in accordance with the present disclosure including a securement tie and an endotracheal tube.

To release the endotracheal tube 4 from the tube fastener 10, the second end region 24 of the securement tie 18 is first removed from the retention clip 27. The pawl 40 may then be actuated by applying a downward force on the raised region 42, thus causing the catch region 44 of the pawl 40 to unclamp and disengage from the teeth 46 of the tie 18. The tie 18 may then be pulled back through the slot 26 to release the endotracheal tube 4. The securement tie 18 includes a generally C-shaped cutout disposed proximate the teeth 46 at the first end region 22 of the tie. The C-shaped cutout defines a grip or pull flap 48 configured to be pulled on in order to correspondingly move the securement tie 18 downward through the slot 26 in order to unwrap the tie 18 from around the endotracheal tube 4. As shown in FIG. 10, when the securement tie 18 is wrapped around the endotracheal tube 4, the grip flap 48 protrudes from a second surface 49 of the tie so that a user can easily grasp it. When the securement tie 18 lies flat, i.e., when the tie is not wrapped around the endotracheal tube 4, the grip flap 48 remains disposed within the C-shape cutout on the tie such that the grip flap is substantially flush with the second surface 49 of the tie, as shown in FIG. 12.

Additionally, the tube fastener 10 may include a bite block 52 to prevent restriction of airflow through the endotracheal tube 4. During intubation, a patient may occasionally bite down on an endotracheal tube 4, thus restricting air flow through the endotracheal tube 4. A bite block 52 made from a more rigid material may be positioned around the endotracheal tube 4 and between the patient's teeth to protect the endotracheal tube 4. The bite block 52 may be made of the same material as the tube holder base 20.

Referring again to FIGS. 4-10, the bite block 52 may be coupled to a rear end region 54 of the tube holder base 20. The bite block 52 extends from the tube holder base 20 towards the patient when the endotracheal tube holder device 2 is secured to the patient's face. The bite block 52 is comprised of a generally tubular wall having a substantially cylindrical shape. The bite block 52 may have an opening 56 extending along the length of the bite block 52 to allow an endotracheal tube 4 to be slid into the bite block 52.

The bite block 52 may be integral with the tube fastener 10, such that the tube fastener 10 and the bite block 52 are a single piece. For example, the tube fastener 10 comprising the tube holder base 20, the lever arms 14, the pawl 40, and the bite block 52 may be fabricated from the same material, and furthermore may be formed through a single molding process. In other implementations, the bite block 52 may be a separate element from the tube fastener 10. For instance, the bite block 52 may be secured to the tube fastener 10 using an adhesive or a mechanical fastener, among other securement means. An inner surface 66 of the bite block 52 defines a channel 62 extending along the length of the bite block 52. The channel 62 may be configured to receive additional passageways, such as accessory lines or suction lines, that accompany the endotracheal tube 4 in order to prevent restriction of such additional passageways.

Figure 9:
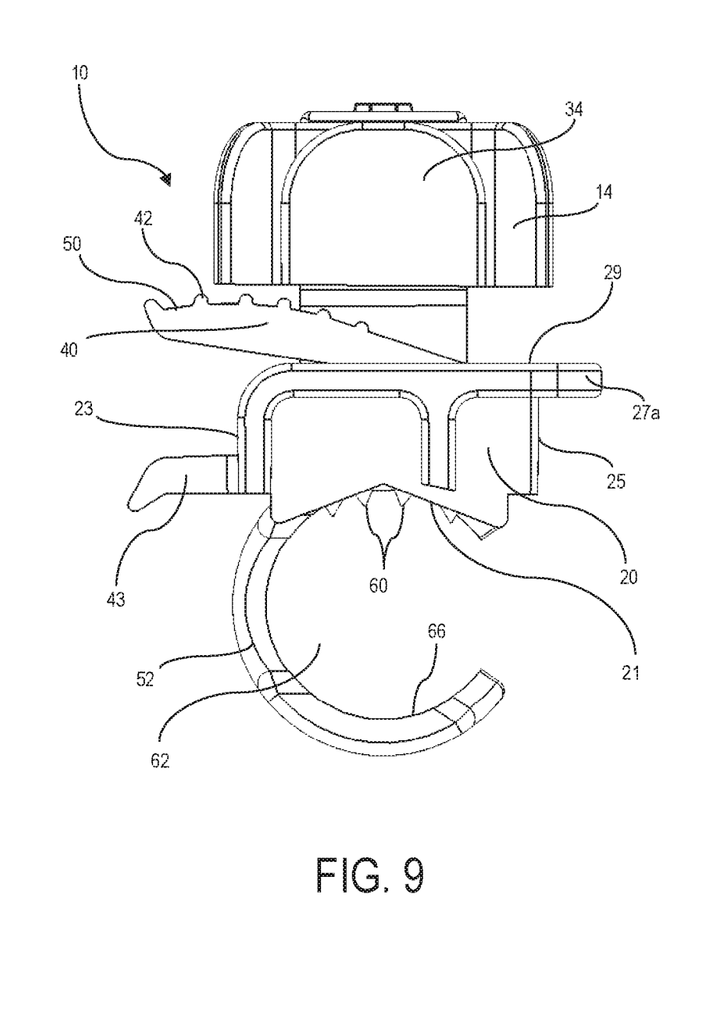
FIG. 9 is a front elevation view of the tube fastener in accordance with the present disclosure.

Reference will now be made to FIG. 9, which illustrates a front view of the tube fastener 10 and the bite block 52, and FIG. 10, which shows an endotracheal tube 4 secured to the tube fastener 10 via the securement tie 18. The raised region 42 of the pawl 40 is located towards the first side 23 of the tube holder base 20, while the catch region 44 of the pawl 40 is located towards the second side region 25 of the tube holder base 20. Although hidden from view, the slot 26 is also located towards the second side region 25 of the tube holder base 20, and is defined between the pawl 40 and tube fastener 10. A bottom surface 21 of the tube holder base 20 defines a substantially V-shaped catch for receiving the endotracheal tube to mitigate unwanted movement of the endotracheal tube relative to the tube holder base 20. The bottom surface 58 of the tube holder base 20 may also include a plurality of projecting barbs 60 configured to engage an endotracheal tube 4 for increased securement.

Accordingly, the substantially V-shaped bottom surface 21 of the tube holder base 20 may include a plurality of barbs 60 to engage an endotracheal tube 4 and help prevent lateral or rotational movement of the endotracheal tube 4. Each of the plurality of barbs 60 may vary in size and shape, or each barb may be the same size and shape. Moreover, the plurality of barbs 60 may be disposed on the bottom surface 21 of the tube holder base 20 in a variety of patterns. In some implementations, the barbs 60 may be substantially conical in shape and with slightly rounded tips at their ends to prevent puncturing the endotracheal tube 4.

Figure 13:
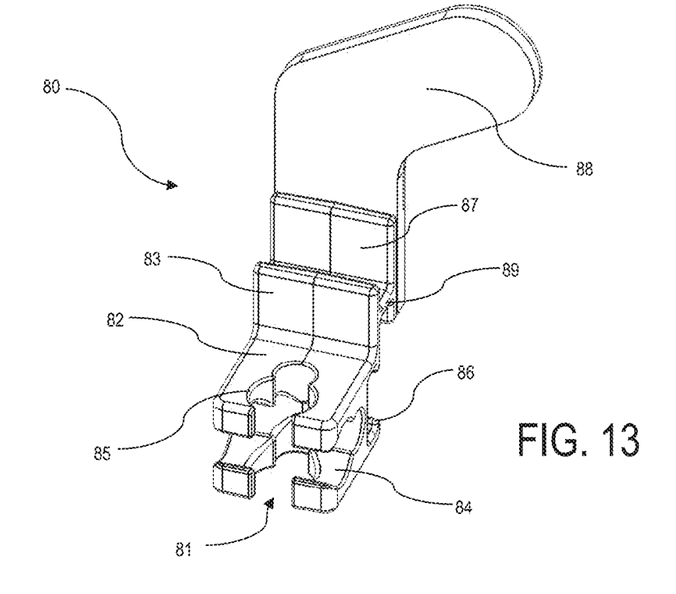
FIG. 13 is a perspective view of an auxiliary clip according to an aspect of the present disclosure.
Figure 14:
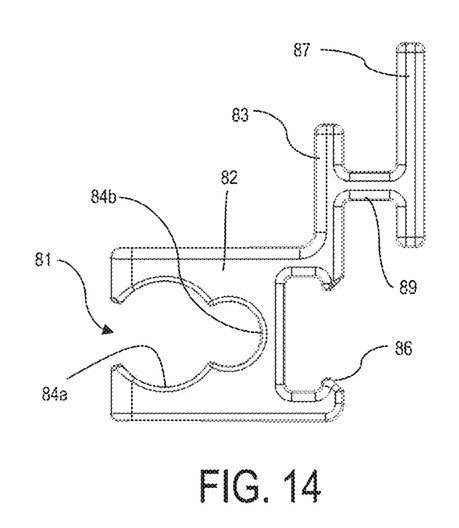
FIG. 14 is a side elevation view of the auxiliary clip illustrated in FIG. 13.
Figure 15:
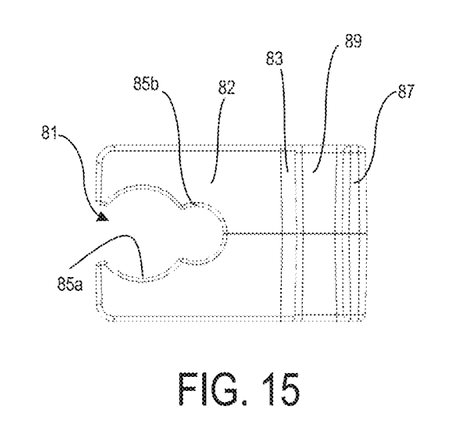
FIG. 15 is a top plan view of the auxiliary clip illustrated in FIG. 13.

FIGS. 13-15 illustrate an implementation of one of the auxiliary clips 80 depicted in FIGS. 1 and 2. The auxiliary clip 80 is configured to stabilize the support rail 6 on the patient's face. The auxiliary clip 80 is also configured to hold an accessory device 90, such as a nasogastric tube or other accessory line, relative to the support rail 6. The auxiliary clip 80 includes a clip base 82 having a rear surface that defines a positioning clip 86. The positioning clip 86 is configured to removably engage the support rail 6 by snapping or sliding onto the exterior portion 28 of the rail, such that the auxiliary clip is detachable from the rail. Further, the auxiliary clip 80 is slidably movable along the length of the support rail 6. A stabilizer wall 83 extends vertically upward from the rear surface of the clip base 82 and is connected to a substantially vertical support wall 87 by an extension bridge 89 disposed therebetween.

The auxiliary clip 80 may include a stabilizer pad 88 attached to the support wall 87 and configured to contact and adhere to a patient's nose, and/or a region of a patient's cheek adjacent to the patient's nose. The stabilizer pad 88 may have a vertical pad portion and slanted pad portion oriented to contact a corresponding left or right side of the patient's nose and/or cheek. For example, FIG. 13 shows an auxiliary clip having a stabilizer pad 88 that includes a vertical pad portion and a slanted pad portion configured to contact a left side of the patient's nose and cheek, respectively. Other implementations of the stabilizer pad 88 may include various shapes sufficient to contact a patient's face, such as symmetrical circular or rectangular pad portions configured to interchangeably contact either the left or right side of the patient's nose and/or cheek. For instance, the stabilizer pad 88 may include pad portions configured to contact the bridge of a patient's nose.

The stabilizer pad 88 may be made of a hydrocolloid dressing, foam, a combination thereof, or other skin compliant material. Each stabilizer pad 88 includes a skin contacting surface that may have an adhesive applied thereto to improve adherence of the pads 88 to the patient's skin. Moreover, each stabilizer pad 88 may also include a peelable backing liner for preserving the adhesive when the stabilizer pads 88 are not adhered to the patient. The stabilizer pads 88 may be flat, and further may be configured to become contoured to match the shape of a patient's face.

The clip base 82 further includes a horizontal accessory clip 84 and/or a vertical accessory clip 85 configured to releasably retain an accessory device 90 horizontally and/or vertically, respectively. A front surface of the clip base 82 defines an opening 81 configured to receive the accessory device 90 within the horizontal and vertical accessory clips 84, 85.

Moreover, the clip base 82 includes a first side surface and a second side surface that each have horizontal accessory clip portions. Similarly, the clip base 82 includes a top surface and a bottom surface that each have vertical accessory clip portions. In particular, as illustrated in FIG. 14, each horizontal accessory clip 84 may include a first horizontal accessory clip portion 84*a* and a second horizontal accessory clip portion 84*b*, wherein the first horizontal accessory clip portion 84*a* is larger than the second horizontal accessory clip portion 84*b* in order to accommodate accessory tubes of various shapes and sizes. Similarly, as illustrated in FIG. 15, each vertical accessory clip 85 may include a first vertical accessory clip portion 85*a* and a second vertical accessory clip portion 85*b*, wherein the first vertical accessory clip portion 85*a* is larger than the second vertical accessory clip portion 85*b* in order to accommodate accessory tubes of various shapes and sizes. The front surface of the stabilizer base 82 defines an opening cutout 81 configured to allow an accessory tube to be slid into a corresponding accessory clip 84, 85. In some aspects, the horizontal and vertical accessory clips 84, 85 may be identical and configured to hold accessory devices of various sizes, such as nasogastric tubes having an outer diameter (and French size) of 3.2 mm OD (10 Fr), 4.0 mm OD (12 Fr), 4.7 mm OD (14 Fr), 5.3 mm OD (16 Fr), 6.0 mm OD (18 Fr), and 6.6 mm OD (20 Fr).

Figure 16:
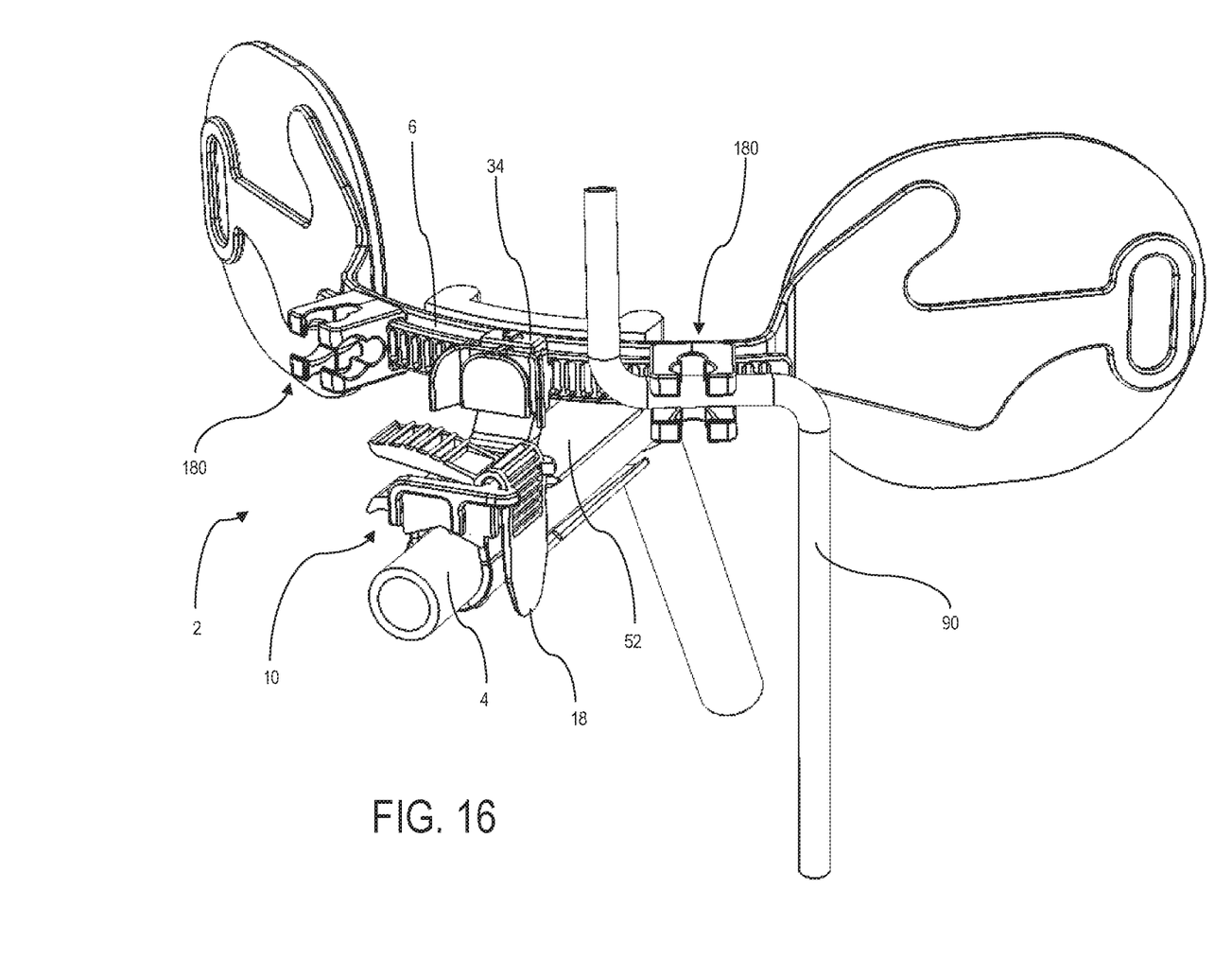
FIG. 16 is a perspective view of an endotracheal tube holder device holding an endotracheal tube and an accessory tube, and having an auxiliary clip according another aspect of the present disclosure.
Figure 17:
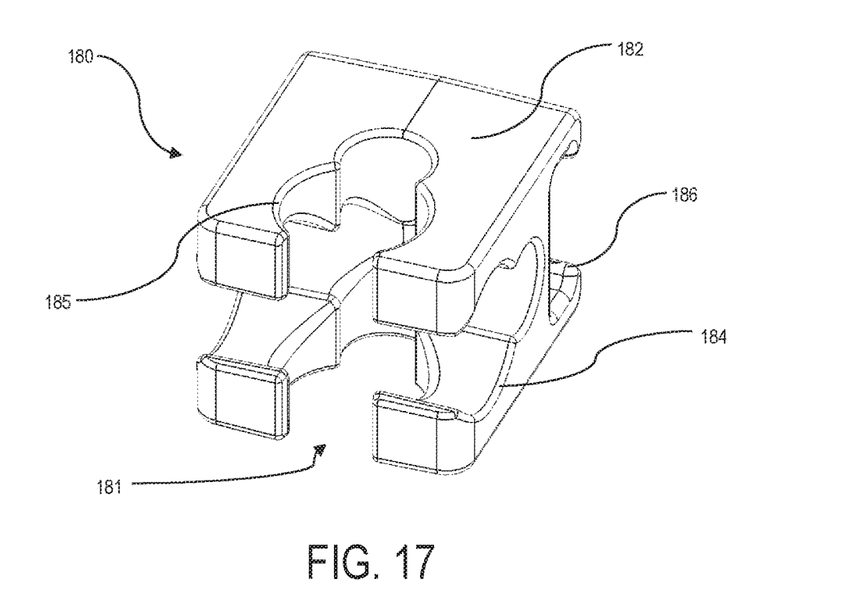
FIG. 17 is a perspective view of an auxiliary clip according to another aspect of the present disclosure.
Figure 18:
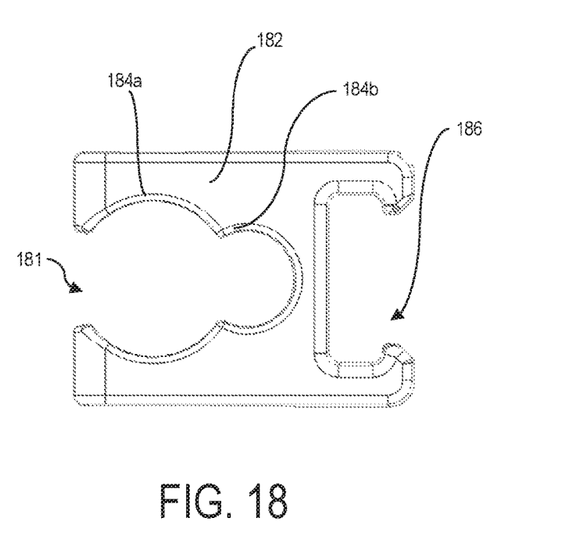
FIG. 18 is a side elevation view of the auxiliary clip illustrated in FIG. 17.
Figure 19:
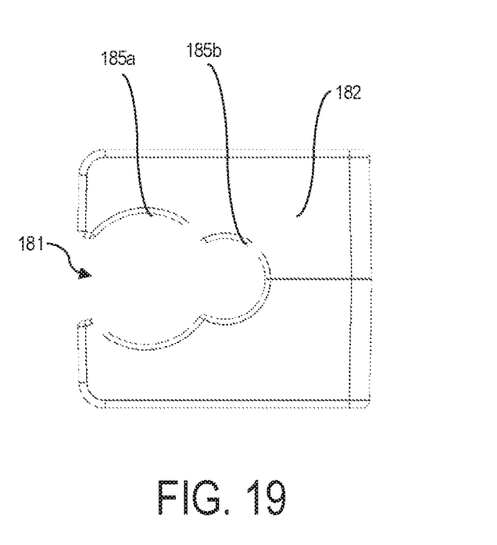
FIG. 19 is a top plan view of the auxiliary clip illustrated in FIG. 17.

Referring to FIG. 16, the endotracheal tube holder device 2 is shown having another implementation of an auxiliary clip 180 removably attached to the support rail 6. The auxiliary clip 180 is configured to hold an accessory device 90, such as an nasogastric tube or other accessory line, relative to the support rail 6 and a patient's face. As shown in FIGS. 17-19, the auxiliary clip 180 includes a clip base 182 having a rear surface that defines a positioning clip 186. The positioning clip 186 is configured to removably engage the support rail 6 by snapping or sliding onto the exterior portion 28 of the rail, such that the auxiliary clip is detachable from the rail. Further, the auxiliary clip 180 is slidably movable along the length of the support rail 6. The clip base 182 further includes a horizontal accessory clip 184 and/or a vertical accessory clip 185 configured to releasably retain the accessory device 90. A front surface of the clip base 182 defines an opening 181 configured to receive the accessory device 90 within the horizontal and vertical accessory clips 184, 185.

Further, the clip base 182 includes a first side surface and a second side surface that each have horizontal accessory clip portions. Similarly, the clip base 182 includes a top surface and a bottom surface that each have vertical accessory clip portions. In particular, as illustrated in FIG. 18, each horizontal accessory clip 184 may include a first horizontal accessory clip portion 184*a* and a second horizontal accessory clip portion 184*b*, wherein the first horizontal accessory clip portion 184*a* is larger than the second horizontal accessory clip portion 184*b* in order to accommodate accessory tubes of various shapes and sizes. Similarly, as illustrated in FIG. 19, each vertical accessory clip 185 may include a first vertical accessory clip portion 185*a* and a second vertical accessory clip portion 185*b*, wherein the first vertical accessory clip portion 185*a* is larger than the second vertical accessory clip portion 185b in order to accommodate accessory tubes of various shapes and sizes. In some aspects, the horizontal and vertical accessory clips 184, 185 may be identical and configured to hold accessory devices of various sizes, such as nasogastric tubes having an outer diameter (and French size) of 3.2 mm OD (10 Fr), 4.0 mm OD (12 Fr), 4.7 mm OD (14 Fr), 5.3 mm OD (16 Fr), 6.0 mm OD (18 Fr), and 6.6 mm OD (20 Fr).

While the endotracheal tube holder device has been described in terms of what may be considered to be specific aspects, the present disclosure is not limited to the disclosed aspects. Additional modifications and improvements to the endotracheal tube holder device may be apparent to those skilled in the art. As such, this disclosure is intended to cover various modifications and similar arrangements included within the spirit and scope of the claims, the scope of which should be accorded the broadest interpretation so as to encompass all such modifications and similar structures. The present disclosure should be considered as illustrative and not restrictive.

What is claimed is:

1. An apparatus for securely holding an endotracheal tube, the apparatus comprising:
   a support rail having opposite ends and an exterior portion defining a plurality of retention grooves at least partially along a length of the support rail between the opposite ends, the support rail configured to be placed above a lip of a patient;
   an auxiliary clip coupled to the support rail and slidably movable along the length of the support rail between the opposite ends, the auxiliary clip configured to hold an accessory device relative to a face of the patient, and the auxiliary clip comprising a clip base having a front surface defining an opening configured to receive the accessory device, and a rear surface defining a positioning clip configured to removably engage the support rail; and
   a tube fastener coupled to the support rail and slidably movable along the length of the support rail between the opposite ends, the tube fastener including:
      a tube holder base having a first side region and a spaced apart second side region;
      an adjustment clip coupled to the tube holder base, the adjustment clip configured to releasably engage the exterior portion of the support rail for laterally repositioning the tube holder base along the support rail between the opposite ends; and
      a securement tie configured to be wrapped around a portion of the endotracheal tube, the securement tie having a first end region coupled to the first side region of tube holder base, and a second end region configured to secure to the second side region of the tube holder base.

2. The apparatus of claim 1, wherein the clip base further includes a horizontal accessory clip and a vertical accessory clip configured to releasably retain the accessory device horizontally and vertically, respectively.

3. The apparatus of claim 2, wherein the horizontal accessory clip includes a first horizontal accessory clip portion and a second horizontal accessory clip portion, the first horizontal accessory clip portion being larger than the second horizontal accessory clip portion, and wherein the vertical accessory clip includes a first vertical accessory clip portion and a second vertical accessory clip portion, the first vertical accessory clip portion being larger than the second vertical accessory clip portion.

4. The apparatus of claim 1, wherein the auxiliary clip is further configured to stabilize the support rail on the face of the patient.

5. The apparatus of claim 4, wherein the auxiliary clip further includes a stabilizer pad configured to contact and adhere to a nose of the patient and/or a region of a cheek of the patient adjacent to the nose of the patient.

6. The apparatus of claim 5, wherein the stabilizer pad comprises a skin contacting surface including a skin compliant adhesive.

7. The apparatus of claim 1, wherein the accessory device is a nasogastric tube.

8. The apparatus of claim 1, further comprising a retention clip extending from the second side region of the tube holder base for retaining the securement tie.

9. The apparatus of claim 1, wherein the securement tie further comprises a plurality of teeth disposed between the first and second end regions.

10. The apparatus of claim 9, wherein the securement tie further includes a grip flap disposed between the first end region and the plurality of teeth for pulling the securement tie away from the second side region of the tube holder base.

11. The apparatus of claim 1, wherein the tube holder base further includes a bottom surface configured to engage a portion of the endotracheal tube.

12. The apparatus of claim 11, wherein the bottom surface of the tube holder base includes a plurality of barbs configured to engage the endotracheal tube.

13. The apparatus of claim 11, wherein the bottom surface of the tube holder base defines a substantially V-shaped catch configured to contact the endotracheal tube and minimize displacement of the endotracheal tube relative to the tube holder base.

14. The apparatus of claim 9, wherein the tube fastener further comprises a movable pawl configured to engage at least one of the plurality of teeth of the securement tie to secure the tie around the endotracheal tube.

15. The apparatus of claim 14, wherein the tube holder base further comprises a slot configured to receive the second end region of the securement tie such that the second end region of the securement tie is pulled past the pawl through the slot to secure the endotracheal tube to the tube holder base.

16. The apparatus of claim 14, further comprising a fixed grip tab extending from a first side region of the tube holder base and disposed proximate the movable pawl.

17. The apparatus of claim 1, further comprising an adhesive tape applied to a first surface of the securement tie at the first end region, wherein the first surface of the tie is configured to contact a portion of the endotracheal tube.

18. The apparatus of claim 1, wherein the tube fastener further comprises a bite block coupled to the tube holder base and configured to extend into a mouth of a patient, and wherein the bite block has a substantially cylindrical shape defining an axial opening along an entirety of a length of the bite block.

19. A kit, comprising:
   the apparatus for holding an endotracheal tube according to claim 1;
   an endotracheal tube; and
   a nasogastric accessory tube.

20. An apparatus for securely holding an endotracheal tube, the apparatus comprising:
   a support rail having opposite ends and an exterior portion defining a plurality of retention grooves at least partially along a length of the support rail between the opposite ends, the support rail configured to be placed above a lip of a patient;

an auxiliary clip coupled to the support rail and slidably movable along the length of the support rail between the opposite ends, the auxiliary clip configured to hold an accessory device relative to a face of the patient; and a tube fastener coupled to the support rail and slidably movable along the length of the support rail between the opposite ends, the tube fastener including:
   a tube holder base having a first side region and a spaced apart second side region;
   an adjustment clip coupled to the tube holder base, the adjustment clip configured to releasably engage the exterior portion of the support rail for laterally repositioning the tube holder base along the support rail between the opposite ends; and
   a securement tie configured to be wrapped around a portion of the endotracheal tube, the securement tie having a first end region coupled to the first side region of tube holder base, and a second end region configured to secure to the second side region of the tube holder base;

wherein the auxiliary clip further comprises a clip base having a front surface defining an opening configured to receive the accessory device, the clip base including a horizontal accessory clip and a vertical accessory clip configured to releasably retain the accessory device horizontally and vertically, respectively, wherein the horizontal accessory clip includes a first horizontal accessory clip portion and a second horizontal accessory clip portion, the first horizontal accessory clip portion being larger than the second horizontal accessory clip portion, and wherein the vertical accessory clip includes a first vertical accessory clip portion and a second vertical accessory clip portion, the first vertical accessory clip portion being larger than the second vertical accessory clip portion.

* * * * *